United States Patent
Tampo et al.

(10) Patent No.: US 6,726,632 B2
(45) Date of Patent: Apr. 27, 2004

(54) ARTERIOSCLEROSIS-DEGREE EVALUATING APPARATUS

(75) Inventors: Akira Tampo, Komaki (JP); Toshihiko Ogura, Komaki (JP); Kiyoyuki Narimatsu, Komaki (JP)

(73) Assignee: Colin Corporation, Komaki (JP)

( * ) Notice: Subject to any disclaimer, the term of this patent is extended or adjusted under 35 U.S.C. 154(b) by 69 days.

(21) Appl. No.: 10/155,985

(22) Filed: May 29, 2002

(65) Prior Publication Data
US 2003/0083580 A1 May 1, 2003

(30) Foreign Application Priority Data
Oct. 29, 2001 (JP) .................................. 2001-331089

(51) Int. Cl.$^7$ ................................. A61B 5/02
(52) U.S. Cl. ..................... 600/481; 600/485; 600/504
(58) Field of Search ............................ 600/300, 481, 600/485, 490, 500, 504, 508, 520

(56) References Cited
U.S. PATENT DOCUMENTS

| | | | |
|---|---|---|---|
| 4,617,937 A | * 10/1986 | Peel et al. | 600/493 |
| 4,807,638 A | * 2/1989 | Sramek | 600/485 |
| 5,772,600 A | * 6/1998 | Kahn et al. | 600/494 |
| 6,315,734 B1 | * 11/2001 | Nunome | 600/500 |

FOREIGN PATENT DOCUMENTS

EP  1 050 267 A1  11/2000

* cited by examiner

Primary Examiner—Robert L. Nasser
Assistant Examiner—Patricia Mallari
(74) Attorney, Agent, or Firm—Oliff & Berridge, PLC

(57) ABSTRACT

An apparatus for evaluating a degree of arteriosclerosis of a living subject, the apparatus including a blood-pressure measuring device which measures a systolic and a diastolic blood pressure of the subject, a pulse-wave-propagation-velocity-related-information obtaining device which obtains pulse-wave-propagation-velocity-related information that is related to a velocity at which a pulse wave propagates through an artery of the subject, a display device, and a control device which controls the display device to display, in a two-dimensional graph defined by a first axis indicative of blood pressure and a second axis indicative of pulse-wave-propagation-velocity-related information, at least one symbol indicating two positions one of which corresponds to the systolic blood pressure measured by the blood-pressure measuring device and the pulse-wave-propagation-velocity-related information obtained by the pulse-wave-propagation-velocity-related-information obtaining device, and the other of which corresponds to the diastolic blood pressure measured by the blood-pressure measuring device and the obtained pulse-wave-propagation-velocity-related information.

12 Claims, 6 Drawing Sheets

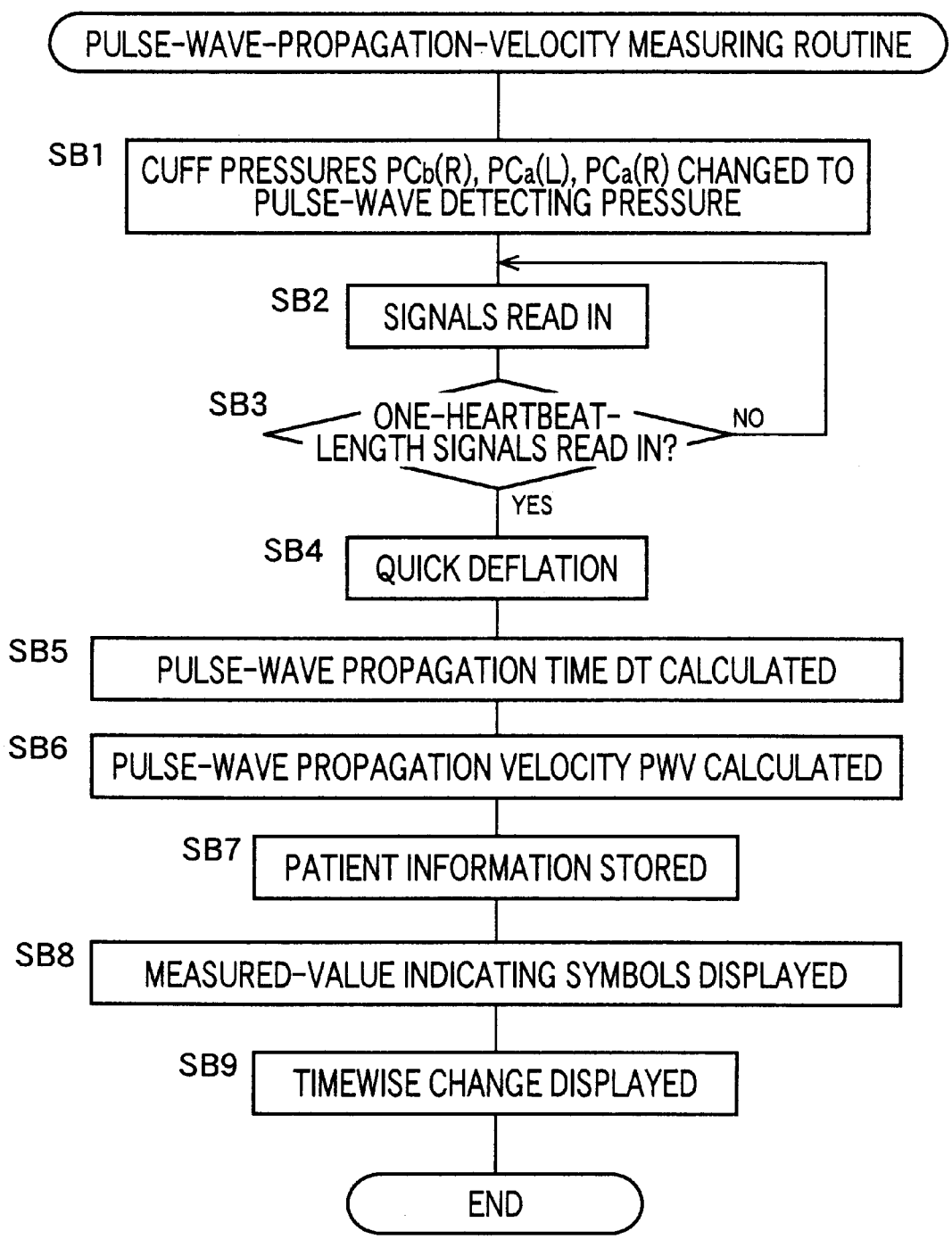

ARTERIOSCLEROSIS-DEGREE EVALUATING APPARATUS

BACKGROUND OF THE INVENTION

1. Field of the Invention

The present invention relates to an arteriosclerosis-degree evaluating apparatus for evaluating an arteriosclerosis degree of a living subject, and particularly to an arteriosclerosis-degree evaluating apparatus for evaluating an arteriosclerosis degree of a subject based on pulse-wave-propagation-velocity-related information that is related to a velocity at which a pulse wave propagates through an artery of the subject; such as pulse-wave propagation velocity itself, or pulse-wave propagation time.

2. Related Art Statement

The harder a blood vessel is, the faster a pulse wave propagates through the vessel. Thus, it is known that arteriosclerosis can be diagnosed based on pulse-wave-propagation-velocity-related information. It is a common practice to employ pulse-wave propagation velocity as the pulse-wave-propagation-velocity-related information. If a measured pulse-wave propagation velocity is higher than a reference value, advanced arteriosclerosis may be diagnosed. In many cases, arteriosclerosis is related to hypertension, and there is such a tendency that the higher the arteriosclerosis is, the higher the blood pressure is. Accordingly, a patient whose hypertension and advanced arteriosclerosis have been diagnosed, is treated using a medicine, such as antihypertensive drug, to lower the blood pressure and the pulse-wave propagation velocity.

The purpose of the treatment using the medicine is to lower the systolic blood pressure down to a normal value (e.g., a value not higher than 140 mmHg) and lower the pulse-wave propagation velocity down to a normal value, which is variable depending on a portion of the patient from which the velocity is measured. For example, in the case where the pulse-wave propagation velocity is measured from an upper arm and an ankle of the patient, a normal value of the velocity is, e.g., not higher than 1,400 cm/sec.

If the antihypertensive drug is used to lower the systolic blood pressure, then the diastolic blood pressure is also lowered. However, if the diastolic blood pressure is excessively lowered, the patient may fall in a dangerous condition. Thus, it is needed to control an amount of administration of the drug to lower the systolic blood pressure and the pulse wave propagation velocity but not to excessively lower the diastolic blood pressure. In particular, a patient who suffers advanced arteriosclerosis is observed such that a pulse pressure, i.e., a difference between the systolic and diastolic blood pressure is large. Accordingly, when the systolic blood pressure of the patient is clinically lowered, then it is needed to take care not to excessively lower the diastolic blood pressure.

However, there has conventionally been only such an arteriosclerosis-degree evaluating apparatus which can just display respective values of systolic blood pressure, diastolic blood pressure, and pulse-wave propagation velocity. Thus, it is not easy for a medical person such as a doctor or a nurse to judge, at a glance, whether all of the systolic blood pressure, diastolic blood pressure, and pulse-wave propagation velocity are normal. In some cases, though the systolic blood pressure and the pulse-wave propagation velocity are carefully observed, the diastolic blood pressure may be overlooked.

SUMMARY OF THE INVENTION

It is therefore an object of the present invention to provide an arteriosclerosis-degree evaluating apparatus which can easily and reliably monitor pulse-wave-propagation-velocity-related information, systolic blood pressure, and diastolic blood pressure of a living subject who is undergoing medication against arteriosclerosis.

The above object has been achieved by the present invention. According to the present invention, there is provided an apparatus for evaluating a degree of arteriosclerosis of a living subject, the apparatus comprising a blood-pressure measuring device which measures a systolic and a diastolic blood pressure of the subject; a pulse-wave-propagation-velocity-related-information obtaining device which obtains pulse-wave-propagation-velocity-related information that is related to a velocity at which a pulse wave propagates through an artery of the subject; a display device; and a control device which controls the display device to display, in a first two-dimensional graph defined by a first axis indicative of blood pressure and a second axis indicative of pulse-wave-propagation-velocity-related information, two symbols at respective positions one of which corresponds to the systolic blood pressure measured by the blood-pressure measuring device and the pulse-wave-propagation-velocity-related information obtained by the pulse-wave-propagation-velocity-related-information obtaining device, and the other of which corresponds to the diastolic blood pressure measured by the blood-pressure measuring device and said obtained pulse-wave-propagation-velocity-related information.

In the present arteriosclerosis-degree evaluating apparatus, the control device, i.e., a graph displaying means controls the display device to display, in the two-dimensional graph defined by the axis indicative of blood pressure and the axis indicative of pulse-wave-propagation-velocity-related information, two measured-value indicating symbols at respective positions one of which corresponds to the systolic blood pressure measured by the blood-pressure measuring device and the pulse-wave-propagation-velocity-related information obtained by the pulse-wave-propagation-velocity-related-information obtaining device, and the other of which corresponds to the diastolic blood pressure measured by the blood-pressure measuring device and the obtained pulse-wave-propagation-velocity-related information. Thus, a medical person can instantaneously recognize, from the respective positions of the measured-value indicating symbols displayed in the two-dimensional graph, the pulse-wave-propagation-velocity-related information and the systolic and diastolic blood pressure of the subject, and accordingly can easily and reliably monitor the pulse-wave-propagation-velocity-related information and the systolic and diastolic blood pressure.

Preferably, the control device or the graph displaying means controls the display device to display, in the first two-dimensional graph, a pre-set normal area corresponding to a normal blood-pressure range and a normal pulse-wave-propagation-velocity-related-information range, a pre-set alert area corresponding to at least one of an alert blood-pressure range and an alert pulse-wave-propagation-velocity-related-information range, and a pre-set danger area corresponding to at least one of a danger blood-pressure range and a danger pulse-wave-propagation-velocity-related-information range.

According to this feature, if all the measured-value indicating symbols fall within the normal area, then the medical person can judge that all the pulse-wave-propagation-velocity-related information and the systolic and diastolic blood pressure are normal. If a portion of the measured-value indicating symbols falls within the alert area, the medical person can judge that attention is needed for at least one of the pulse-wave-propagation-velocity-related information and the systolic and diastolic blood pressure. And, if a portion of the measured-value indicating symbols falls within the danger area, the medical person can judge that treatment is needed for at least one of the pulse-wave-propagation-velocity-related information and the systolic and diastolic blood pressure. Thus, the present apparatus or the medical person can more reliably monitor the pulse-wave-propagation-velocity-related information and the systolic and diastolic blood pressure.

Preferably, the pulse-wave-propagation-velocity-related-information obtaining device obtains a piece of pulse-wave-propagation-velocity-related information from the subject, at a substantially same time as a time when the blood-pressure measuring device measures systolic and diastolic blood pressure values of the subject in each of a plurality of measuring operations, the arteriosclerosis-degree evaluating apparatus further comprises a memory device which accumulatively stores a set of subject information including the systolic and diastolic blood pressure values measured, and the piece of pulse-wave-propagation-velocity-related information obtained, in the each of the measuring operations, and the control device comprises a time-wise-change displaying means for controlling the display device to display, in a second two-dimensional graph defined by a third axis indicative of blood pressure and a fourth axis indicative of pulse-wave-propagation-velocity-related information, respective symbols at respective positions which respectively correspond to the sets of subject information accumulatively stored by the memory device.

According to this feature, the memory device accumulatively stores a plurality of sets of subject information each set of which includes systolic and diastolic blood pressure values measured, and a piece of pulse-wave-propagation-velocity-related information obtained, in a corresponding one of a plurality of measuring operations, and the time-wise-change displaying means controls the display device to display, in a two-dimensional graph defined by an axis indicative of blood pressure and an axis indicative of pulse-wave-propagation-velocity-related information, respective measured-value indicating symbols at respective positions which respectively correspond to the sets of subject information accumulatively stored by the memory device. Thus, the medical person can easily and instantaneously recognize, from the plurality of measured-value indicating symbols displayed in the two-dimensional graph, respective time-wise changes of the systolic and diastolic blood pressure and the pulse-wave-propagation-velocity-related information. Based on those time-wise changes and an amount of administration of drug until then, the medical person can judge whether the amount of the drug is appropriate.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 6 is a flow chart representing a pulse-wave-propagation-velocity measuring routine according to which the essential control functions of the control device, shown in FIG. 2, are operated.

DETAILED DESCRIPTION OF PREFERRED EMBODIMENTS

Figure 1:
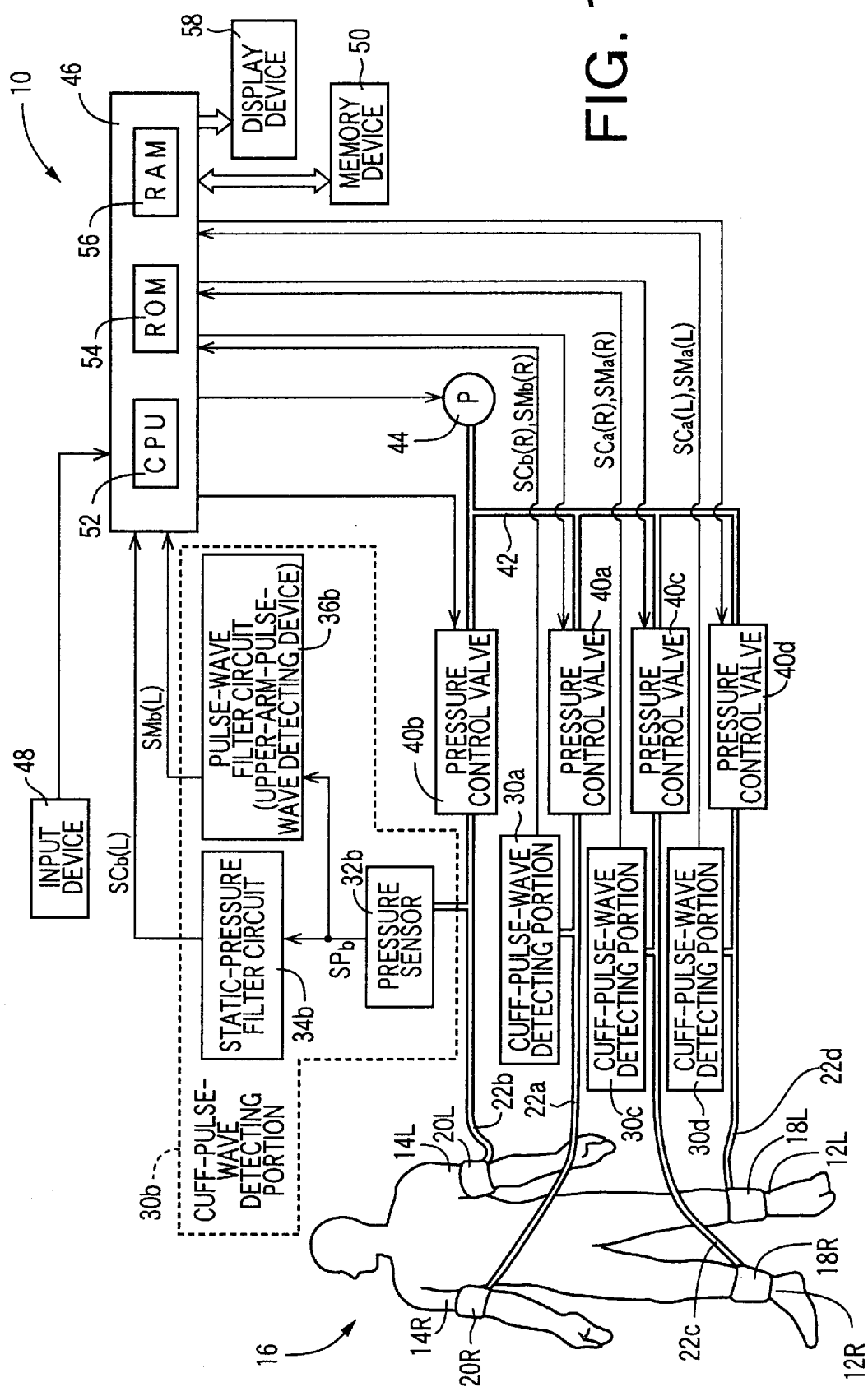
FIG. 1 is a diagrammatic view for explaining a construction of an arteriosclerosis-degree evaluating apparatus to which the present invention is applied.

Hereinafter, there will be described an embodiment of the present invention in detail by reference to the drawings. FIG. 1 shows a diagrammatic view for explaining a construction of an arteriosclerosis-degree evaluating apparatus 10 to which the present invention is applied.

The present apparatus includes two ankle cuffs 18R, 18L which are wound around right and left ankles 12R, 12L of a patient 16, respectively, and two upper-arm cuffs 20R, 20L which are wound around right and left upper arms 14R, 14L of the patient 16, respectively. Each of the cuffs 18, 20 functions as a pressing band which presses a portion of the patient around which the each cuff is wound, and includes a belt-like outer bag which is formed of a non-stretchable material such as cloth or polyester; and a rubber bag accommodated in the outer bag.

The two upper-arm cuffs 20R, 20L are connected via respective pipings 22a, 22b to respective cuff-pulse-wave detecting portions 30a, 30b and respective pressure control valves 40a, 40b; and the two ankle cuffs 18R, 18L are connected via respective pipings 22c, 22d to respective cuff-pulse-wave detecting portions 30c, 30d and respective pressure control valves 40c, 40d. Since the four cuff-pulse-wave detecting portions 30a, 30b, 30c, 30d have an identical construction, and the four pressure control valves 40a, 40b, 40c, 40d have an identical construction, the cuff-pulse-wave detecting portion 30b and the pressure control valve 40b to which the upper-arm cuff 20L is connected will be described below as respective representatives of the four detecting devices 30 and the four control valves 40.

The cuff-pulse-wave detecting portion 30b includes a pressure sensor 32b, a static-pressure filter circuit 34b, and a pulse-wave filter circuit 36b, and the piping 22b is connected to the pressure sensor 32b. The pressure control valve 40b is connected via a piping 42 to an air pump 44.

The pressure control valve 40b is arranged such that the control valve 40b is selectively switchable to one of four positions, that is, a pressure-supply position in which the control valve 40b adjusts a pressure of a compressed air supplied from the air pump 44 and supplies the pressure-adjusted air to the upper-arm cuff 20L, a pressure-maintain position in which the control valve 40b maintains the pressure in the upper-arm cuff 20L, a slow-deflation position in which the control valve 40b slowly decreases the pressure in the upper-arm cuff 20L, and a quick-deflation position in which the control valve 40b quickly decreases the pressure in the upper-arm cuff 20L.

The pressure sensor 32b detects the pressure in the upper-arm cuff 20L, and supplies a pressure signal, $SP_b(L)$, representing the detected pressure, to the static-pressure filter circuit 34b and the pulse-wave filter circuit 36b. The static-pressure filter circuit 34b includes a low-pass filter which extracts, from the pressure signal $SP_b(L)$, a leftupper-arm cuff-pressure signal, $SC_b(L)$, representing a left-upper-arm cuff pressure, $PC_b(L)$, as a static component of the detected pressure. The filter circuit 34b supplies the left-upper-arm cuff-pressure signal $SC_b(L)$ to an electronic control device 46 via an A/D (analog-to-digital) converter, not shown.

The pulse-wave filter circuit 36b includes a band-pass filter which extracts, from the pressure signal $SP_b(L)$, a left-upper-arm pulse-wave signal, $SM_b(L)$, representing a left-upper-arm pulse wave $W_b(L)$ as an oscillatory component of the detected pressure that has prescribed frequencies. The filter circuit 36b supplies the left-upper-arm pulse-wave signal $SM_b(L)$ to the control device 46 via an A/D converter, not shown. Since the left-upper-arm pulse-wave signal $SM_b(L)$ represents the left-upper-arm pulse wave $W_b(L)$ that is produced by an artery of the left upper arm 14L pressed by the upper-arm cuff 20L, the pulse-wave filter circuit 36b functions as an upper-arm-pulse-wave detecting device. Similarly, a pulse-wave filter circuit 36a of the cuff-pulse-wave detecting portion 30a functions as an upper-arm-pulse-wave detecting device which provides a right-upper-arm pulse-wave signal $SM_b(R)$ representing a right-upper-arm pulse wave $W_b(R)$ as an oscillatory pressure wave that is produced by an artery of the right upper arm 14R pressed by the upper-arm cuff 20R; a pulse-wave filter circuit 36c of the cuff-pulse-wave detecting portion 30c functions as an ankle-pulse-wave detecting device which provides a right-ankle pulse-wave signal $SM_a(R)$ representing a right-ankle pulse wave $W_a(R)$ as an oscillatory pressure wave that is produced by an artery of the right ankle 12R pressed by the ankle cuff 18R; and a pulse-wave filter circuit 36d of the cuff-pulse-wave detecting portion 30d functions as an ankle-pulse-wave detecting device which provides a left-ankle pulse-wave signal $SM_a(L)$ representing a left-ankle pulse wave $W_a(L)$ as an oscillatory pressure wave that is produced by an artery of the left ankle 12L pressed by the ankle cuff 18L. The upper-arm cuff 20L, the cuff-pulse-wave detecting portion 30b, the pressure control valve 40b, and the air pump 44 cooperate with one another to provide an upper-arm blood-pressure measuring device 40L. Similarly, the upper-arm cuff 20R, the cuff-pulse-wave detecting portion 30a, the pressure control valve 40a, and the air pump 44 cooperate with one another to provide another upper-arm blood-pressure measuring device 40R.

In the following description, the pressing pressure of the upper-arm cuff 20R will be expressed as the right-upper-arm cuff pressure $PC_b(R)$; the signal extracted by the static-pressure filter circuit 34a will be expressed as the right-upper-arm cuff-pressure signal $SC_b(R)$; the signal extracted by the pulse-wave filter circuit 36a will be expressed as the right-upper-arm pulse-wave signal $SM_b(R)$; the pressing pressure of the upper-arm cuff 20L will be expressed as the left-upper-arm cuff pressure $PC_b(L)$; the signal extracted by the static-pressure filter circuit 34b will be expressed as the left-upper-arm cuff-pressure signal $SC_b(L)$; the signal extracted by the pulse-wave filter circuit 36c will be expressed as the left-upper-arm pulse-wave signal $SM_b(L)$; the right-upper-arm cuff pressure $PC_b(R)$ or the left-upper-arm cuff pressure $PC_b(L)$ will be expressed simply as the upper-arm cuff pressure $PC_b$, when they need not be distinguished from each other; and the right-upper-arm pulse-wave signal $SM_b(R)$ or the left-upper-arm pulse-wave signal $SM_b(L)$ will be expressed simply as the upper-arm pulse wave $SM_b$, when they need not be distinguished from each other. In addition, the pressing pressure of the ankle cuff 18R will be expressed as the right-ankle cuff pressure $PC_a(R)$; the signal extracted by the static-pressure filter circuit 34c will be expressed as the right-ankle cuff-pressure signal $SC_a(R)$; the signal extracted by the pulse-wave filter circuit 36c will be expressed as the right-ankle pulse-wave signal $SM_a(R)$; the pressing pressure of the ankle cuff 18L will be expressed as the left-ankle cuff pressure $PC_a(L)$; the signal extracted by the static-pressure filter circuit 34d will be expressed as the left-ankle cuff-pressure signal $SC_a(L)$; the signal extracted by the pulse-wave filter circuit 36d will be expressed as the left-ankle pulse-wave signal $SM_a(L)$; the right-ankle cuff pressure $PC_a(R)$ or the left-ankle cuff pressure $PC_a(L)$ will be expressed simply as the ankle cuff pressure $PC_a$, when they need not be distinguished from each other; and the right-ankle pulse-wave signal $SM_a(R)$ or the left-ankle pulse-wave signal $SM_a(L)$ will be expressed simply as the ankle pulse wave $SM_a$, when they need not be distinguished from each other.

An input device 48 which functions as a patient identifying device or a height inputting device, includes input keys, not shown, which are for inputting an identification number identifying the patient, and a height of the patient, and supplies respective signals representing the input identification number and height, to the control device 46. A memory device 50 is provided by a well-known memory such as a magnetic disc, a magnetic tape, a volatile semiconductor memory, or a non-volatile semiconductor memory, and stores, in respective prescribed memory areas, the blood-pressure values BP and pulse-wave propagation velocity PWV determined by the control device 46, and the patient's identification number and height input through the input device 48.

The electronic control device 46 is essentially provided by a microcomputer including a CPU (central processing unit) 52, a ROM (read only memory) 54, a RAM (random access memory) 56, and an I/O (input-and-output) port, not shown. The CPU 52 processes signals according to the control programs pre-stored in the ROM 54, while utilizing the temporary-storage function of the RAM 56, and outputs, from the I/O port, drive signals to the air pump 44 and the pressure control valves 40 (40a, 40b, 40c, 40d). In addition, the CPU 52 determines blood-pressure values BP and a pulse-wave propagation velocity PWV of the patient, and controls what is displayed by a display device 58.

Figure 2:
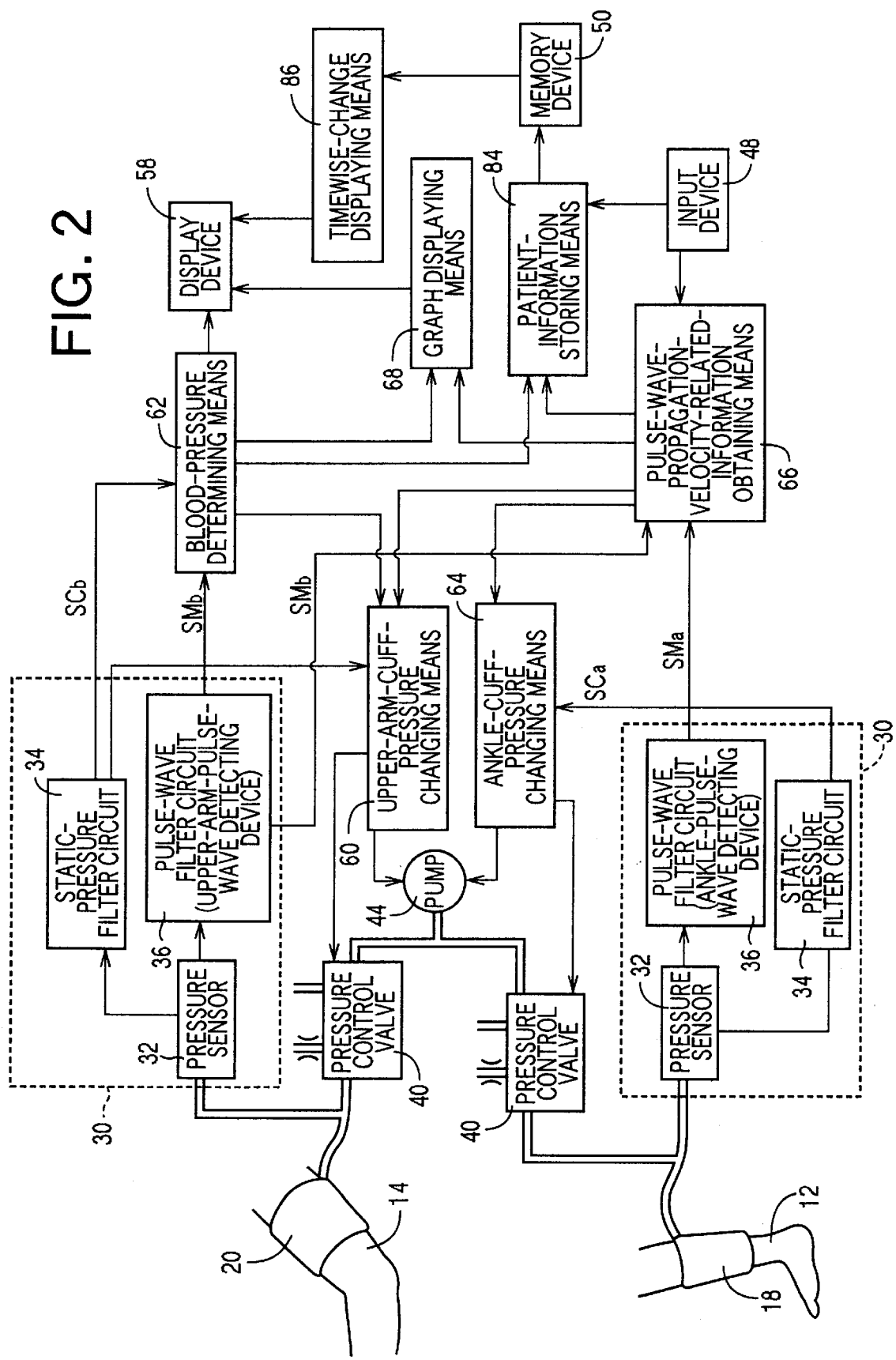
FIG. 2 is a diagrammatic view for explaining essential control functions of an electronic control device of the apparatus of FIG. 1.

FIG. 2 is a diagrammatic view for explaining essential control functions of the electronic control device 46. In the present arteriosclerosis-degree evaluating apparatus 10, the two upper-arm cuffs 20L, 20R are worn on the left and right upper arms 14L, 14R, respectively; the two pulse-wave detecting portions 30b, 30a and the two pressure control valves 40b, 40a are connected to the left and right upper-arm cuffs 20L, 20R, respectively; the two ankle cuffs 18L, 18R are worn on the left and right ankle 18L, 18R, respectively; and the two pulse-wave detecting portions 30d, 30c and the two pressure control valves 40d, 40c are connected to the left and right ankle cuffs 18L, 18R, respectively. However, the various control functions of the control device 46 are all common to the left and right upper arms 14, or the left and right ankles 12, and may be used with respect to both the left and right arms 14 or ankles 12, or only one of the left and right arms 14 or ankles 12 (i.e., either the left arm 14 or ankle 12, or the right arm 14 or ankle 12). Thus, FIG. 2 shows only one upper-arm cuff 20 that represents both, or either one, of the left and right upper-arm cuffs 20, and only one ankle cuff 18 that represents both, or either one, of the left and right ankle cuffs 18.

An upper-arm-cuff-pressure changing means 60 is operated, according to a command signal supplied thereto from a blood-pressure determining means 62, described later, to control the air pump 44, and the pressure control valve 40 connected to the upper-arm cuff 20, based on the upper-arm cuff-pressure signal $SC_b$ supplied from the static-pressure filter circuit 34 of the cuff-pulse-wave detecting portion 30 connected to the upper-arm cuff 20, so that the upper-arm cuff pressure $PC_b$ is quickly increased up to a pre-set target pressure value, $PC_M$, (e.g., 180 mmHg), and subsequently is slowly decreased at a rate of 3 mmHg/sec and, after blood-pressure values BP have been determined, the upper-arm cuff pressure $PC_b$ is deflated down to an atmospheric pressure. In addition, the upper-arm-cuff-pressure changing means 60 is operated, according to a command signal supplied thereto from a pulse-wave-propagation-velocity-related-information obtaining means 66, described later, to change the upper-arm cuff pressure $PC_b$ to a pre-set upper-arm-pulse-wave detecting pressure, e.g., 60 mmHg, that is lower than a diastolic blood pressure of the upper arm 14. The upper-arm-pulse-wave detecting pressure is pre-set at a value which assures that the upper-arm pulse-wave signal $SM_b$ extracted by the pulse-wave filter circuit 36 has a sufficiently great magnitude.

The blood-pressure determining means 62 determines, based on change of respective amplitudes of successive heartbeat-synchronous pulses of the upper-arm pulse wave $W_b$ represented by the upper-arm pulse-wave signal $SM_b$ continuously supplied during the slow decreasing of the upper-arm cuff pressure $PC_b$ under the control of the upper-arm-cuff-pressure changing means 60, a systolic blood-pressure value $BP_{SYS}$, a diastolic blood-pressure value $BP_{DIA}$, and a mean blood-pressure value $BP_{MEAN}$ of the patient, according to well-known oscillometric method, and controls the display device 58 to display the thus determined systolic blood-pressure value $BP_{SYS}$, etc.

An ankle-cuff-pressure changing means 64 is operated, according to a command signal supplied from the pulse-wave-propagation-velocity-related-information obtaining means 66, described later, to control the air pump 44, and the pressure control valve 40 connected to the ankle cuff 18, based on the ankle cuff-pressure signal $SC_a$ supplied from the static-pressure filter circuit 34 of the cuff-pulse-wave detecting portion 30 connected to the ankle cuff 18, so that the ankle cuff pressure $PC_a$ is changed to a pre-set ankle-pulse-wave detecting pressure, e.g., 60 mmHg, that is lower than a diastolic blood pressure of the ankle 12. The ankle-pulse-wave detecting pressure is pre-set at a value which assures that the ankle pulse-wave signal $SM_a$ extracted by the pulse-wave filter circuit 36 has a sufficiently great magnitude, and may be equal to the pre-set upper-arm-pulse-wave detecting pressure.

The pulse-wave-propagation-velocity-related-information obtaining means 66 obtains pulse-wave-propagation-velocity-related information, based on the upper-arm pulse-wave signal $SM_b$ extracted by the pulse-wave filter circuit 36 of the cuff-pulse-wave detecting portion 30 connected to the upper-arm cuff 20, and the ankle pulse-wave signal $SM_a$ extracted by the pulse-wave filter circuit 36 of the cuff-pulse-wave detecting portion 30 connected to the ankle cuff 18.

More specifically described, the information obtaining means 66 determines, as a pulse-wave propagation time, DT (sec), a time difference between a time of detection of a prescribed point, e.g., a rising point or a maximal point, of a heartbeat-synchronous pulse of the upper-arm pulse wave $W_b$ represented by the upper-arm pulse-wave signal $SM_b$, and a time of detection of a prescribed of the ankle pulse wave $W_a$ represented by the ankle pulse-wave signal $SM_a$ that corresponds to the prescribed point of the upper-arm pulse wave $W_b$. Since the upper-arm pulse-wave signal $SM_b$ may be either one of the left and right upper-arm pulse-wave signals $SM_b(L)$, $SM_b(R)$, and the ankle pulse-wave signal $SM_a$ may be either one of the left and right ankle pulse-wave signals $SM_a(L)$, $SM_a(R)$, there are four possible combinations to use one of the two signals $SM_b(L)$, $SM_b(R)$ and one of the two signals $SM_a(L)$, $SM_a(R)$ so as to determine the pulse-wave propagation time DT. Any one of the four combinations may be employed.

Alternatively, the information obtaining means 66 may additionally determine a propagation distance, L, based on the patient's height H input through the input device 48, according to a relationship between height H and propagation distance L, represented by the following Expression 1 pre-stored in the ROM 54, and finally determine a pulse-wave propagation velocity, PWV, (cm/sec) based on the thus determined propagation distance L and pulse-wave propagation time DT, according to the following Expression 2 pre-stored in the ROM 54:

$$L = \alpha H + \beta \qquad \text{(Expression 1)}$$

where α and β are constants that are experimentally obtained.

$$PWV = L/DT \qquad \text{(Expression 2)}$$

The propagation distance L is substantially equal to a difference between a distance between the patient's heart and the upper arm 14 on which the upper-arm cuff 20 is worn, and a distance between the patient's heart and the ankle 12 on which the ankle cuff 18 is worn.

The present arteriosclerosis-degree evaluating apparatus 10 is used to observe respective changes of blood pressure and pulse-wave-propagation-velocity-related information that may result from administration of a drug. Thus, it is preferred that the pulse-wave-propagation-velocity-related-information obtaining means 66 obtain pulse-wave-propagation-velocity-related information at substantially the same time as a time when the blood-pressure determining means 62 determines blood-pressure values BP. Here, the phrase "substantially the same time" is used to mean that both the pulse-wave-propagation-velocity-related information and the blood-pressure values are influenced by the same administration of drug.

Figure 3:
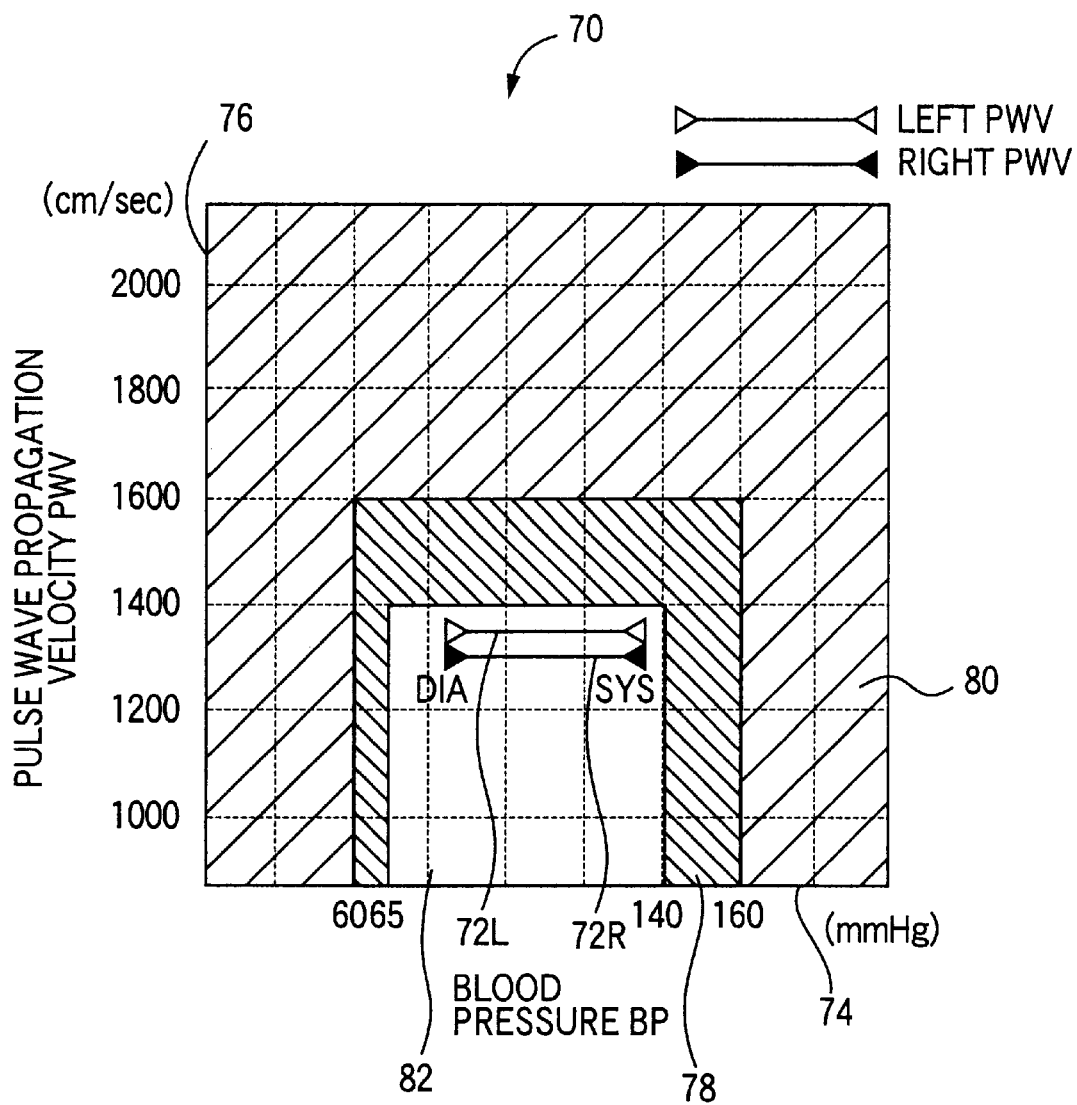
FIG. 3 is a view showing an example of a two-dimensional graph which is displayed, on a display device, by a graph displaying means shown in FIG. 2.

A graph displaying means 68 controls the display device 58 to display a two-dimensional graph 70, as shown in FIG. 3, and additionally display two measured-value indicating symbols 72L, 72R in the two-dimensional graph 70. The two-dimensional graph 70 is defined by a blood-pressure axis 74 and a pulse-wave-propagation-velocity axis 76. Each of the measured-value indicating symbols 72L, 72R is a straight segment one of opposite ends of which corresponds to the diastolic blood-pressure value $BP_{DIA}$ determined by the blood-pressure determining means 62 and the pulse-wave propagation velocity PWV calculated by the pulse-wave-propagation-velocity-related-information obtaining means 66, and the other end of which corresponds to the systolic blood-pressure value $BP_{SYS}$ determined by the determining means 62 and the pulse-wave propagation velocity PWV calculated by the obtaining means 66. The symbol 72L as one of the two symbols 72L, 72R shown in FIG. 34 represents the blood-pressure values BP(L) measured from the left upper arm 14L, and the left pulse-wave propagation velocity PWV(L) determined based on the left-ankle pulse-wave signal $SM_a(L)$; and the other symbol 72R represents the blood-pressure values BP(R) measured from the right upper arm 14R, and the right pulse-wave propagation velocity PWV(R) determined based on the right-ankle pulse-wave signal $SM_a(R)$. However, it is not necessary to display the two symbols 72L, 72R, but it is possible to display a single symbol 72.

The two-dimensional graph 70 includes an alert area 78 corresponding to at least one of an alert range of blood pressure BP and an alert range of pulse-wave propagation velocity PWV; and a danger area 80 corresponding to at least one of a danger range of blood pressure BP and a danger range of pulse-wave propagation velocity PWV. Each alert range indicates that attention is needed, and each danger range indicates that treatment is need. A normal area 82 corresponding to a normal range of blood pressure BP and a normal range of pulse-wave propagation velocity PWV is defined by the remaining area of the two-dimensional graph 70 other than the alert area 78 and the danger area 80.

A patient-information storing means 84 stores, in a prescribed memory area of the memory device 50, a set of patient information including the patient's identification number and height supplied from the input device 48, the blood-pressure values BP determined by the blood-pressure determining means 62, and the pulse-wave-propagation-velocity-related information obtained by the pulse-wave-propagation-velocity-related-information obtaining means 66.

Figure 4:
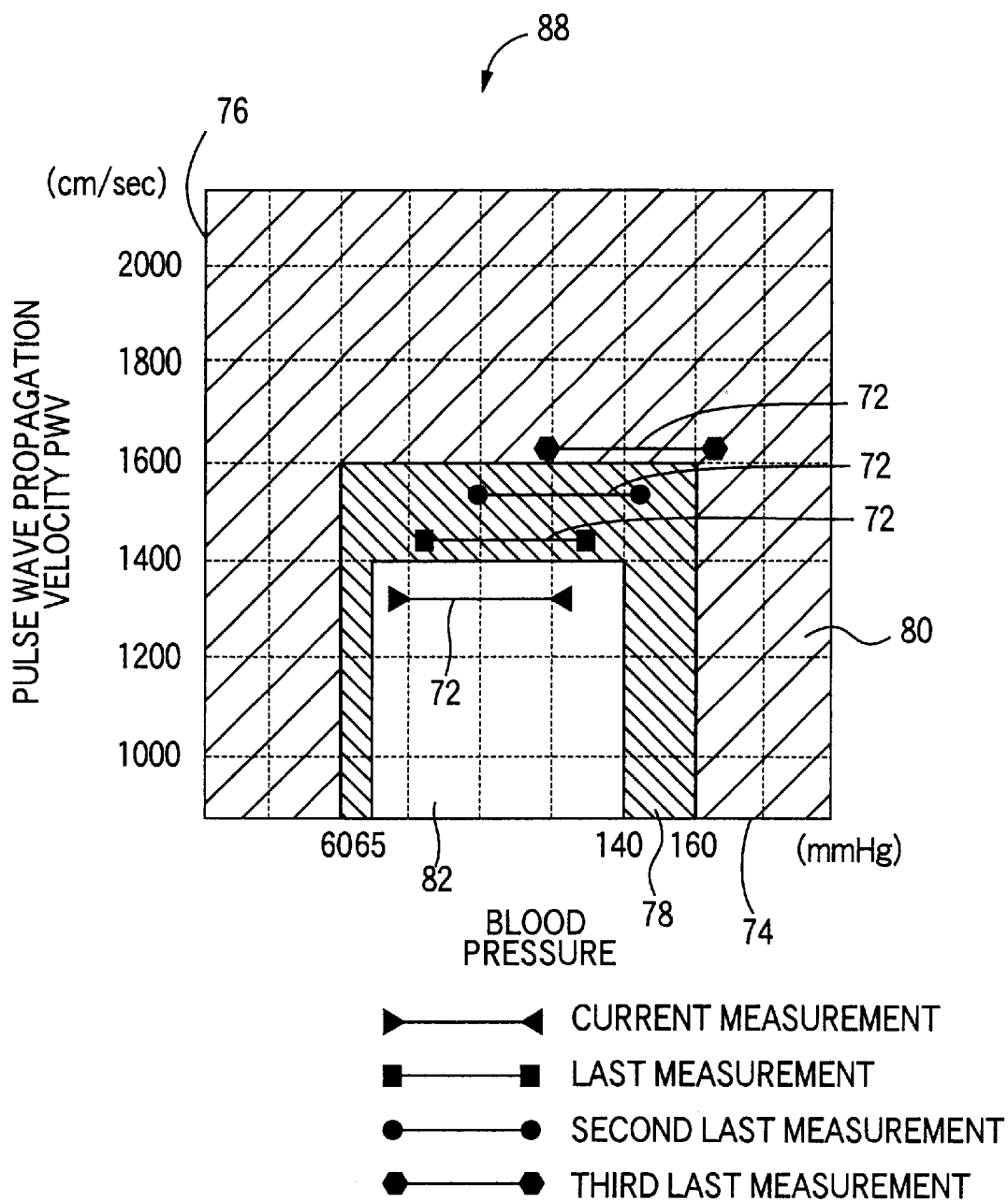
FIG. 4 is a view showing an example of another two-dimensional graph which is displayed, on the display device, by a time-wise-change displaying means shown in FIG. 2.

A timewise-change displaying means 86 controls the display device 58 to display, in addition to the first two-dimensional graph 70 displayed by the graph displaying means 68, a second two-dimensional graph 88 similar to the first graph 70, and display, in the second graph 88 (or the first graph 70), not only a measured-value indicating symbol 72 corresponding to a current measuring operation, but also one or more measured-value indicating symbols 72 corresponding to one or more past measuring operations, i.e., one or more sets of patient information stored in the memory device 50. FIG. 4 shows an example of the two-dimensional graph 88 displayed by the timewise-change displaying means 86.

Figure 5:
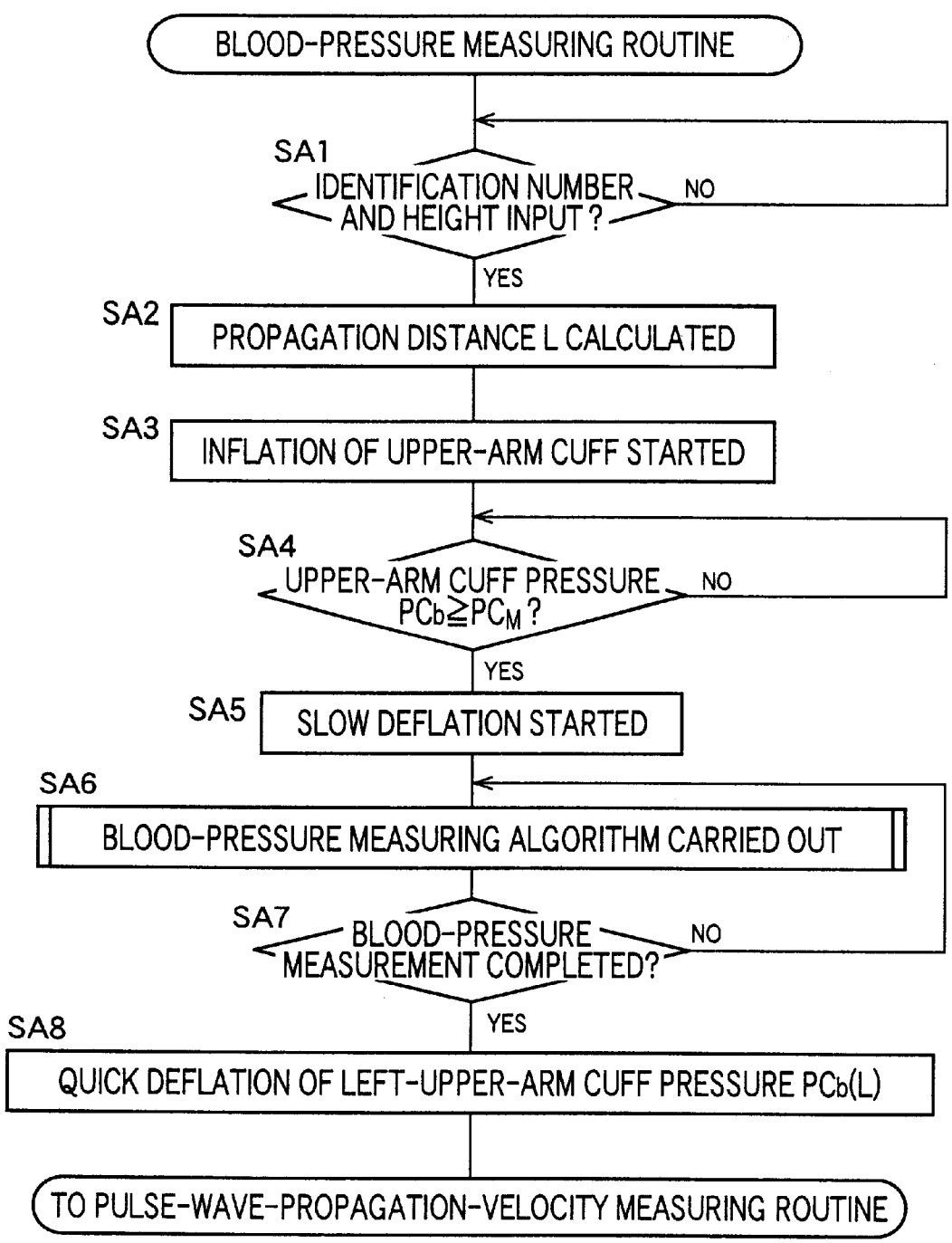
FIG. 5 is a flow chart representing a blood-pressure measuring routine according to which the essential control functions of the control device, shown in FIG. 2, are operated.

FIGS. 5 and 6 are flow charts representing the essential control functions of the electronic control device 46, shown in FIG. 2. FIG. 5 shows a blood-pressure measuring routine, and FIG. 6 shows a pulse-wave-propagation-velocity measuring routine following the routine of FIG. 5.

First, the blood-pressure measuring routine of FIG. 5 will be described. At Step SA1 (hereinafter, "Step" is omitted, if appropriate), the control device 46 judges whether the patient's identification number and height have been inputted, i.e., whether signals representing the patient's identification number and height have been supplied thereto from the input device 48. If a negative judgment is made at SA1, SA1 is repeated till a positive judgment is made. Meanwhile, if a positive judgment is made at SA1, the control goes to SA2 and the following steps. At SA2, the control device determines a propagation distance L based on the patient's height H supplied from the input device 48, according to the above-mentioned Expression 1.

Then, at SA3, the control device operates the air pump 44 and switches the pressure control valves 40a, 40b connected to the left and right upper-arm cuffs 20R, 20L to their pressure-supply positions, so that quick inflation of the left and right upper-arm cuff pressures $PC_b(L)$, $PC_b(R)$ is started. Subsequently, at SA4, the control device judges whether the upper-arm cuff pressures $PC_b(L)$, $PC_b(R)$ have reached a target pressure value $P_{CM}$ pre-set at 180 mmHg. Step SA4 is repeated while a negative judgment is made. Meanwhile, if a positive judgment is made at SA4, the control goes to SA5 to stop the air pump 44 and switch the pressure control valves 40a, 40b to their slow-deflation positions so that slow deflation of the upper-arm cuff pressures $PC_b(L)$, $PC_b(R)$ at a rate of 3 mmHg/sec is started.

Then, the control goes to SA6 corresponding to the blood-pressure determining means 62. At SA6, the control device determines, based on change of respective amplitudes of successive heartbeat-synchronous pulses of the left-upper-arm pulse wave $W_b(L)$ represented by the left-upper-arm pulse-wave signal $SM_b(L)$ continuously obtained during the slow decreasing of the left-upper-arm cuff pressure $PC_b(L)$, a systolic blood-pressure value $BP_{SYS}(L)$, a diastolic blood-pressure value $BP_{DIA}(L)$, and a mean blood-pressure value $BP_{MEAN}(L)$ of the left upper arm 14L, according to well-known oscillometric method, and additionally determines, based on change of respective amplitudes of successive heartbeat-synchronous pulses of the right-upper-arm pulse wave $W_b(R)$ represented by the right-upper-arm pulse-wave signal $SM_b(R)$ continuously obtained during the slow decreasing of the right-upper-arm cuff pressure $PC_b(R)$, a systolic blood-pressure value $BP_{SYS}(R)$, a diastolic blood-pressure value $BP_{DIA}(R)$, and a mean blood-pressure value $BP_{MEAN}(R)$ of the right upper arm 14R, according to the well-known oscillometric method.

Then, at SA7, the control device judges whether the determination of blood-pressure values BP has been completed at SA6. Since diastolic blood-pressure values $BP_{DIA}$ are determined last at SA6, the control judges whether diastolic blood-pressure values $BP_{DIA}$ have been determined. If a positive judgment is made at SA7, the control goes to SA8 to switch the pressure control valve 40b to its quick-deflation position so that the left-upper-arm cuff pressure $PC_b(L)$ is deflated to an atmospheric pressure. Then, the control goes to the pulse-wave-propagation-velocity measuring routine of FIG. 6.

Next, the pulse-wave-propagation-velocity measuring routine of FIG. 6 will be described. First, at SB1, the control device again operates the air pump 44 and controls the pressure control valves 40a, 40c, 40d so that the right-upper-arm cuff pressure $PC_b(R)$ and the left and right ankle cuff pressures $PC_a(L)$, $PC_a(R)$ are changed to the upper-arm-pulse-wave detecting pressure and the ankle-pulse-wave detecting pressure, respectively, each of which is equal to 60 mmHg.

Then, at SB2, the control device reads in the right-upper-arm pulse-wave signal $SM_b(R)$ supplied from the pulse-wave filter circuit 36b of the cuff-pulse-wave detecting portion 30a connected to the upper-arm cuff 14R, and the ankle pulse-wave signals $SM_a(L)$, $SM_a(R)$ supplied from the pulse-wave filter circuits 36d, 36c of the cuff-pulse-wave detecting portions 30d, 30c connected to the left and right ankle cuffs 18L, 18R. Subsequently, at SB3, the control device judges whether the control device has read in respective one-heartbeat lengths of the right-upper-arm pulse-wave signal $SM_b(R)$ and the two ankle pulse-wave signals $SM_a(L)$, $SM_a(R)$. If a negative judgment is made at SB3, SB2 and the following steps are repeated while the reading of those signals are continued.

Meanwhile, if a positive judgment is made at SB3, the control goes to SB4 to switch the pressure control valves 40a, 40c, 40d to their quick-deflation positions, and stop the air pump 44, so that the right-upper-arm cuff pressure $PC_b(R)$ and the left and right ankle cuff pressures $PC_a(L)$, $PC_a(R)$ are decreased down to the atmospheric pressure. In the flow charts of FIGS. 5 and 6, SA3 to SA5, SA8, SB1, and SB4 correspond to the upper-arm-cuff-pressure changing means 60; and SB1 and SB4 correspond to the ankle-cuff-pressure changing means 64.

Then, at SB5, the control device determines respective rising points (i.e., respective minimal points) of the respective one-heartbeat lengths of the upper-arm pulse wave $W_b(R)$ and the left and right ankle pulse waves $W_a(L)$, $W_a(R)$, read in while SB2 and SB3 are repeated. In addition, the control device determines, as a left pulse-wave propagation time DT(L), a time difference between a time of detection of the rising point of the upper-arm pulse wave $W_b$ and a time of detection of the rising point of the left ankle pulse wave $W_a$ (L), and determines, as a right pulse-wave propagation time DT(R), a time difference between the time of detection of the rising point of the upper-arm pulse wave $W_b$ and a time of detection of the rising point of the right ankle pulse wave $W_a$ (R). Then, at SB6, the control device determines a left pulse-wave propagation velocity PWV(L) based on the left pulse-wave propagation time DT(L) determined at SB5 and the propagation distance L determined at SA2 of FIG. 5, according to the above-mentioned Expression 2, and determines a right pulse-wave propagation velocity PWV(R) based on the right pulse-wave propagation time DT(R) determined at SB5 and the propagation distance L, according to Expression 2. In the flow charts of FIGS. 5 and 6, SA2, SB5, and SB6 correspond to the pulse-wave-propagation-velocity-related-information obtaining means 66.

Next, the control goes to SB7 corresponding to the patient-information storing means 84. At SB7, the control device stores, in the memory device 50, a set of patient information including the patient's identification number and height inputted at SA1, the left and right systolic blood-pressure values $BP_{SYS}(L)$, $BP_{SYS}(R)$ and left and right systolic blood-pressure values $BP_{DIA}(L)$, $BP_{DIA}(R)$ determined at SA6, and the left and right pulse-wave propagation velocity values PWV(L), PWV(R) determined at SB6.

Subsequently, the control goes to SB8 corresponding to the graph displaying means 68. As shown in FIG. 3, the control device controls the display device 58 to display the two-dimensional graph 70 and additionally display, in the graph 70, the measured-value indicating symbol 72L corresponding to the left systolic and diastolic blood-pressure values $BP_{SYS}(L)$, $BP_{DIA}(L)$ determined at SA6 and the left pulse-wave propagation velocity PWV(L) determined at SB6, and the measured-value indicating symbol 72R corresponding to the right systolic and diastolic blood-pressure values $BP_{SYS}(R)$, $BP_{DIA}(R)$ determined at SA6 and the right pulse-wave propagation velocity PWV(R) determined at SB6.

Then, the control goes to SB9 corresponding to the timewise-change displaying means 86. As shown in FIG. 4, the control device controls the display device 58 to display the two-dimensional graph 88 and additionally display, in the graph 88, two or more measured-value indicating symbols 72 corresponding to two or more sets of patient information that have been stored, in the memory device 50, for the patient 16 whose blood-pressure values BP and pulse-wave propagation velocity PWV are measured in the current measuring operation. Thus, the display device 58 display respective timewise changes of the blood pressure BP and the pulse-wave propagation velocity PWV of the patient 16.

In the embodiment in which the flow charts of FIGS. 5 and 6 are employed, the control device 46 controls, at SB8 (the graph displaying means 68), the display device 58 to display, in the two-dimensional graph 70 defined by the blood-pressure axis 74 and the pulse-wave-propagation-velocity axis 76, the measured-value indicating symbol 72 having one end at the position corresponding to the systolic blood-pressure value $BP_{SYS}$ determined at SA6 (the blood-pressure determining means 62) and the pulse-wave-propagation velocity PWV determined at SB6 (the pulse-wave-propagation-velocity-related-information obtaining means 66), and having the other end at the position corresponding to the diastolic blood-pressure value $BP_{DIA}$ determined at SA6 (the determining means 62) and the pulse-wave-propagation velocity PWV determined at SB6 (the obtaining means 66). Therefore, a medical person such as a doctor or a nurse can instantaneously recognize, from the position where the symbol 72 is displayed in the two-dimensional graph 70, the pulse-wave-propagation velocity PWV, the systolic blood-pressure value $BP_{SYS}$, and the diastolic blood-pressure value $BP_{DIA}$ of the patient. Thus, the pulse-wave-propagation velocity PWV, the systolic blood-pressure value $BP_{SYS}$, and the diastolic blood-pressure value $BP_{DIA}$ can be easily and reliably monitored.

In addition, in the embodiment in which the flow charts of FIGS. 5 and 6 are employed, the control device controls the display device 58 to display, in the two-dimensional graph 70, the normal area 82 corresponding to corresponding to the normal range of blood pressure BP and the normal range of pulse-wave propagation velocity PWV, the alert area 78 corresponding to at least one of the alert range of blood pressure BP and the alert range of pulse-wave propagation velocity PWV, and the danger area 80 corresponding to at least one of the danger range of blood pressure BP and the danger range of pulse-wave propagation velocity PWV Therefore, if all the measured-value indicating symbols 72 fall within the normal area 82, the medical person can judge that all the pulse-wave-propagation velocity PWV, the systolic blood-pressure value $BP_{SYS}$, and the diastolic blood-pressure value $BP_{DIA}$ are normal. If a portion of the symbols 72 falls within the alert area 78, the person can judge that attention is needed for at least one of the pulse-wave-propagation velocity PWV, the systolic blood-pressure value $BP_{SYS}$, and the diastolic blood-pressure value $BP_{DIA}$; and if a portion of the symbols 72 falls within the danger area 80, the person can judge that treatment is needed for at least one of the pulse-wave-propagation velocity PWV, the systolic blood-pressure value $BP_{SYS}$, and the diastolic blood-pressure value $BP_{DIA}$. Thus, the reliability of monitoring of the pulse-wave-propagation velocity PWV, the systolic blood-pressure value $BP_{SYS}$, and the diastolic blood-pressure value $BP_{DIA}$ is improved.

Moreover, in the embodiment in which the flow charts of FIGS. 5 and 6 are employed, the control device controls, at SB9 (the timewise-change displaying means 86), the display device 58 to display, in the two-dimensional graph 88, two or more measured-value indicating symbols 72, if the memory device 50 stores two or more sets of patient information each set of which includes a pulse-wave-propagation velocity PWV, a systolic blood-pressure value $BP_{SYS}$, and a diastolic blood-pressure value $BP_{DIA}$. Thus, the medical person can easily and instantaneously recognize, from the two or more symbols 72 displayed in the two-dimensional graph 88, the respective timewise changes of the pulse-wave-propagation velocity values PWV, the systolic blood-pressure values $BP_{SYS}$, and the diastolic blood-pressure values $BP_{DIA}$. Based on those timewise changes and the amount of administration of drug till then, the person can judge whether the amount of drug is appropriate.

While the present invention has been described in its preferred embodiment by reference to the drawings, it is to be understood that the invention may otherwise be embodied.

For example, in the illustrated embodiment, the measured-value indicating symbol 72 displayed by the graph displaying means 68 or the timewise-change displaying means 86 is a straight segment whose one end corresponds to the diastolic blood-pressure value $BP_{DIA}$ and the pulse-wave propagation velocity PWV and whose other end corresponds to the systolic blood-pressure value $BP_{SYS}$ and the pulse-wave propagation velocity PWV. However, it is possible to display, as measured-value indicating symbols, only two points corresponding to the two ends of each straight segment 72.

In the illustrated arteriosclerosis-degree evaluating apparatus 10, the cuffs 18, 20 are worn on the ankle 12 and the upper arm 14, respectively, and the pulse-wave-propagation-velocity-related information is obtained based on the respective heartbeat-synchronous signals (i.e., pulse waves) detected from those two portions, i.e., ankle 12 and upper arm 14. However, it is possible to obtain pulse-wave-propagation-velocity-related information based on heartbeat-synchronous signals detected from other portions such as the heart, the neck, wrists, or finger tips, etc. of the patient.

Moreover, in the illustrated embodiment, the blood-pressure determining means 62 determines the blood-pressure values BP based on the change of pressure in the upper-arm cuff 20 worn on the upper arm 14. However, the blood-pressure determining means 62 may be modified to determine blood-pressure values BP based on change of pressure in the ankle cuff 18 worn on the ankle 12. Otherwise, it is possible to wear a cuff on a portion (e.g., a femoral portion) other than the upper arm 14 or the ankle 12 and determine blood-pressure values BP based on change of pressure in the cuff.

It is to be understood that the present invention may be embodied with other changes, improvements and modifications that may occur to a person skilled in the art without departing from the spirit and scope of the invention defined in the appended claims.

What is claimed is:

1. An apparatus for evaluating a degree of arteriosclerosis of a living subject, the apparatus comprising:
    a blood-pressure measuring device which measures a systolic and a diastolic blood pressure of the subject;
    a pulse-wave-propagation-velocity-related-information obtaining device which obtains pulse-wave-propagation-velocity-related information that is related to a velocity at which a pulse wave propagates through an artery of the subject;
    a display device; and
    a control device which controls the display device to display, in a first two-dimensional graph defined by a first axis indicative of blood pressure and a second axis indicative of pulse-wave-propagation-velocity-related information, at least one symbol indicating two positions, one of which corresponds to the systolic blood pressure measured by the blood-pressure measuring device and the pulse-wave-propagation-velocity-related information obtained by the pulse-wave-propagation-velocity-related-information obtaining device, and the other of which corresponds to the diastolic blood pressure measured by the blood-pressure measuring device and said obtained pulse-wave-propagation-velocity-related information;
    wherein the pulse-wave-propagation-velocity-related-information obtaining device obtains a piece of pulse-wave-propagation-velocity-related information from the subject, at a substantially same time as a time when the blood-pressure measuring device measures systolic and diastolic blood pressure values of the subject in each of a plurality of measuring operations, wherein the apparatus further comprises a memory device which accumulatively stores a set of subject information including the systolic and diastolic blood pressure values measured, and the piece of pulse-wave-propagation-velocity-related information obtained, in said each of the measuring operations, and wherein the control device comprises a time-wise-change displaying device for controlling the display device to display, in a second two-dimensional graph defined by a third axis indicative of blood pressure and a fourth axis indicative of pulse-wave-propagation-velocity-related information, respective symbols at respective positions which respectively correspond to the sets of subject information accumulatively stored by the memory device.

2. An apparatus according to claim 1, wherein the blood-pressure measuring device comprises:
    an inflatable cuff which is adapted to be worn on a portion of the subject;
    a pressure changing device that changes a pressure in the cuff; and
    a blood-pressure determining device that determines the systolic and diastolic blood pressure values of the subject based on change of respective amplitudes of a plurality of heartbeat-synchronous pulses obtained from the cuff when the pressure of the cuff is changed by the pressure changing device.

3. An apparatus according to claim 1, wherein the pulse-wave-propagation-velocity-related-information obtaining device comprises:
    a first heartbeat-synchronous-signal detecting device which detects a first heartbeat-synchronous-signal from a first portion of the subject;
    a second heartbeat-synchronous-signal detecting device which detects a second heartbeat-synchronous-signal from a second portion of the subject; and
    a propagation-time determining device that determines, as a pulse-wave-propagation time as a sort of the pulse-wave-propagation-velocity-related information, a time difference between a time of detection of a prescribed point of the first heartbeat-synchronous-signal detected by the first heartbeat-synchronous-signal detecting device and a time of detection of a prescribed point of the second heartbeat-synchronous-signal detected by the second heartbeat-synchronous-signal detecting device.

4. An apparatus according to claim 3, wherein the pulse-wave-propagation-velocity-related-information obtaining device further comprises a velocity determining device that determines, as the pulse-wave-propagation-velocity-related information, the pulse-wave propagation velocity based on the pulse-wave propagation time determined by the propagation-time determining device.

5. An apparatus according to claim 4, wherein the pulse-wave-propagation-velocity-related-information obtaining device further comprises:
    an input device which is operable for inputting a height of the subject;
    a memory which stores a predetermined relationship between subject's height and a propagation distance, the propagation distance being equal to a difference between a first distance between the heart and the first portion of the subject and a second distance between the heart and the second portion of the subject; and a propagation-distance determining device that determines a propagation distance based on the height of the subject input through the input device, according to the predetermined relationship between the subject's height and propagation distance, stored in the memory, wherein the velocity determining device determines the pulse-wave propagation velocity based on the propagation time determined by the propagation-time determining device and the propagation distance determined by the propagation-distance determining device.

6. An apparatus according to claim 1, wherein the control device controls the display device to display, in the first two-dimensional graph, a straight segment whose opposite ends provide two of said at least one symbol.

7. An apparatus for evaluating a degree of arteriosclerosis of a living subject, the apparatus comprising:

a blood-pressure measuring device which measures a systolic and a diastolic blood pressure of the subject;

a pulse-wave-propagation-velocity-related-information obtaining device which obtains pulse-wave-propagation-velocity-related information that is related to a velocity at which a pulse wave propagates through an artery of the subject;

a display device; and a control device which controls the display device to display, in a first two-dimensional graph defined by a first axis indicative of blood pressure and a second axis indicative of pulse-wave-propagation-velocity-related information, at least one symbol indicating two positions, one of which corresponds to the systolic blood pressure measured by the blood-pressure measuring device and the pulse-wave-propagation-velocity-related information obtained by the pulse-wave-propagation-velocity-related-information obtaining device, and the other of which corresponds to the diastolic blood pressure measured by the blood-pressure measuring device and said obtained pulse-wave-propagation-velocity-related information;

wherein the control device controls the display device to display, in the first two-dimensional graph, a pre-set normal area corresponding to a normal blood-pressure range and a normal pulse-wave-propagation-velocity-related-information range, a pre-set alert area corresponding to at least one of an alert blood-pressure range and an alert pulse-wave-propagation-velocity-related-information range, and a pre-set danger area corresponding to at least one of a danger blood-pressure range and a danger pulse-wave-propagation-velocity-related-information range.

8. An apparatus according to claim 7, wherein the control device controls the display device to display, in the first two-dimensional graph, a straight segment whose opposite ends provide two of said at least one symbol.

9. An apparatus according to claim 7, wherein the blood-pressure measuring device comprises:

an inflatable cuff which is adapted to be worn on a portion of the subject;

a pressure changing device that changes a pressure in the cuff; and a blood-pressure determining device that determines the systolic and diastolic blood pressure values of the subject based on change of respective amplitudes of a plurality of heartbeat-synchronous pulses obtained from the cuff when the pressure of the cuff is changed by the pressure changing device.

10. An apparatus according to claim 7, wherein the pulse-wave-propagation-velocity-related-information obtaining device comprises:

a first heartbeat-synchronous-signal detecting device which detects a first heartbeat-synchronous-signal from a first portion of the subject;

a second heartbeat-synchronous-signal detecting device which detects a second heartbeat-synchronous-signal from a second portion of the subject; and a propagation-time determining device that determines, as a pulse-wave propagation time as a sort of the pulse-wave-propagation-velocity-related information, a time difference between a time of detection of a prescribed point of the first heartbeat-synchronous-signal detected by the first heartbeat-synchronous-signal detecting device and a time of detection of a prescribed point of the second heartbeat-synchronous-signal detected by the second heartbeat-synchronous-signal detecting device.

11. An apparatus according to claim 10, wherein the pulse-wave-propagation-velocity-related-information obtaining device further comprises a velocity determining device that determines, as the pulse-wave-propagation-velocity-related information, the pulse-wave propagation velocity based on the pulse-wave propagation time determined by the propagation-time determining device.

12. An apparatus according to claim 11, wherein the pulse-wave-propagation-velocity-related-information obtaining device further comprises:

an input device which is operable for inputting a height of the subject;

a memory which stores a predetermined relationship between the subject's height and a propagation distance, the propagation distance being equal to a difference between a first distance between the heart and the first portion of the subject and a second distance between the heart and the second portion of the subject; and a propagation-distance determining device that determines a propagation distance based on the height of the subject input through the input device, according to the predetermined relationship between the subject's height and propagation distance, stored in the memory, wherein the velocity determining device determines the pulse-wave propagation velocity based on the propagation time determined by the propagation-time determining device and the propagation distance determined by the propagation-distance determining device.

* * * * *